(12) United States Patent
Furman

(10) Patent No.: US 9,037,208 B2
(45) Date of Patent: May 19, 2015

(54) METHOD AND SYSTEM FOR MONITORING A HEALTH CONDITION

(75) Inventor: Dan Gur Furman, Gedera (IL)

(73) Assignee: Cardio Art Technologies, Ltd., Or Yehuda (IL)

( * ) Notice: Subject to any disclaimer, the term of this patent is extended or adjusted under 35 U.S.C. 154(b) by 1042 days.

(21) Appl. No.: 12/119,462

(22) Filed: May 12, 2008

(65) Prior Publication Data

US 2008/0221419 A1 Sep. 11, 2008

Related U.S. Application Data

(63) Continuation-in-part of application No. PCT/IL2006/001416, filed on Dec. 10, 2006.

(60) Provisional application No. 60/748,218, filed on Dec. 8, 2005.

(30) Foreign Application Priority Data

Aug. 30, 2007 (IL) .......................... 185609

(51) Int. Cl.
*A61B 5/0285* (2006.01)
*A61B 5/029* (2006.01)
*A61B 8/06* (2006.01)
*A61B 5/0205* (2006.01)
*A61B 5/0245* (2006.01)
*A61B 8/12* (2006.01)
(Continued)

(52) U.S. Cl.
CPC ................. *A61B 8/06* (2013.01); *A61B 5/0008* (2013.01); *A61B 5/0031* (2013.01); *A61B 5/0205* (2013.01); *A61B 5/0245* (2013.01); *A61B 5/145* (2013.01); *A61B 8/02* (2013.01); *A61B 8/04* (2013.01); *A61B 8/12* (2013.01); *A61N 1/37* (2013.01); *A61N 1/3925* (2013.01)

(58) Field of Classification Search
USPC .......... 600/453, 454, 455, 504, 505, 507, 323
See application file for complete search history.

(56) References Cited

U.S. PATENT DOCUMENTS

| 4,770,177 A | 9/1988 | Schroeppel |
|---|---|---|
| 5,112,869 A | 5/1992 | Watanabe et al. |

(Continued)

FOREIGN PATENT DOCUMENTS

| WO | WO 92/20273 | 11/1992 |
|---|---|---|
| WO | WO 93/17621 | 9/1993 |

(Continued)

OTHER PUBLICATIONS

International Preliminary Report on Patentability on PCT Application No. PCT/IL2006/001416; issued Mar. 10, 2009; 7 pages; International Bureau of WIPO, Geneva, Switzerland.

(Continued)

*Primary Examiner* — Catherine Voorhees
*Assistant Examiner* — Natasha Patel
(74) *Attorney, Agent, or Firm* — Faegre Baker Daniels LLP

(57) ABSTRACT

A system and method for monitoring a health condition are disclosed. The system includes a patient management application, a data store and a monitoring device. The monitoring device includes an optical sensor, a Doppler sensor, and a computing device adapted to provide health parameter values including oxygen saturation of the blood, blood flow, blood pressure, heart rate, and cardiac output.

19 Claims, 7 Drawing Sheets

(51) Int. Cl.
| | |
|---|---|
| A61B 5/00 | (2006.01) |
| A61B 5/145 | (2006.01) |
| A61B 8/02 | (2006.01) |
| A61B 8/04 | (2006.01) |
| A61N 1/37 | (2006.01) |
| A61N 1/39 | (2006.01) |

(56) References Cited

U.S. PATENT DOCUMENTS

| | | |
|---|---|---|
| 5,174,295 A | 12/1992 | Christian et al. |
| 5,218,962 A | 6/1993 | Mannheimer et al. |
| 5,309,916 A | 5/1994 | Hatschek |
| 5,409,009 A | 4/1995 | Olson |
| 5,464,434 A | 11/1995 | Alt |
| 5,488,953 A | 2/1996 | Vilkomerson |
| 5,544,649 A | 8/1996 | David et al. |
| 5,558,092 A | 9/1996 | Unger |
| 5,606,972 A | 3/1997 | Routh |
| 5,713,939 A | 2/1998 | Nedungadi et al. |
| 5,772,589 A | 6/1998 | Bernreuter |
| 5,817,009 A | 10/1998 | Rosenheimer et al. |
| 5,833,603 A | 11/1998 | Kovacs et al. |
| 5,995,208 A | 11/1999 | Sarge et al. |
| 6,053,873 A | 4/2000 | Govari et al. |
| 6,176,832 B1 | 1/2001 | Habu et al. |
| 6,206,835 B1 | 3/2001 | Spillman, Jr. et al. |
| 6,231,516 B1 | 5/2001 | Keilman et al. |
| 6,261,233 B1 | 7/2001 | Kantorovich |
| 6,277,078 B1 | 8/2001 | Porat et al. |
| 6,398,731 B1 | 6/2002 | Mumm et al. |
| 6,409,675 B1 * | 6/2002 | Turcott .................. 600/508 |
| 6,475,153 B1 | 11/2002 | Khair et al. |
| 6,485,418 B2 | 11/2002 | Yasushi et al. |
| 6,609,023 B1 | 8/2003 | Fischell et al. |
| 6,622,322 B1 | 9/2003 | Caveney |
| 6,929,610 B2 | 8/2005 | Forstner |
| 7,004,907 B2 | 2/2006 | Banet et al. |
| 7,125,383 B2 | 10/2006 | Hoctor et al. |
| 7,127,300 B2 | 10/2006 | Mazar et al. |
| 7,179,228 B2 | 2/2007 | Banet |
| 7,238,158 B2 * | 7/2007 | Abend .................. 600/454 |
| 7,238,159 B2 | 7/2007 | Banet et al. |
| 7,267,649 B2 | 9/2007 | Zdeblick et al. |
| 7,272,428 B2 | 9/2007 | Hopman et al. |
| 7,308,292 B2 | 12/2007 | Colvin et al. |
| 7,364,566 B2 * | 4/2008 | Elkins et al. .................. 604/104 |
| 7,396,330 B2 | 7/2008 | Banet et al. |
| 2002/0010390 A1 | 1/2002 | Guice et al. |
| 2002/0095092 A1 | 7/2002 | Kondo et al. |
| 2003/0097068 A1 | 5/2003 | Hossack et al. |
| 2003/0139778 A1 * | 7/2003 | Fischell et al. .................. 607/3 |
| 2004/0106953 A1 | 6/2004 | Yomtov et al. |
| 2004/0167416 A1 | 8/2004 | Lee |
| 2004/0236223 A1 | 11/2004 | Barnes et al. |
| 2005/0096557 A1 * | 5/2005 | Vosburgh et al. .................. 600/509 |
| 2005/0154303 A1 * | 7/2005 | Walker et al. .................. 600/443 |
| 2005/0216199 A1 | 9/2005 | Banet |
| 2005/0228299 A1 | 10/2005 | Banet |
| 2005/0228300 A1 | 10/2005 | Jaime et al. |
| 2005/0245831 A1 | 11/2005 | Banet |
| 2005/0245882 A1 * | 11/2005 | Elkins et al. .................. 604/239 |
| 2005/0261594 A1 | 11/2005 | Banet |
| 2006/0009697 A1 | 1/2006 | Banet et al. |
| 2006/0009698 A1 | 1/2006 | Banet et al. |
| 2006/0100530 A1 | 5/2006 | Kliot et al. |
| 2006/0129038 A1 | 6/2006 | Zelenchuk et al. |
| 2006/0224053 A1 * | 10/2006 | Black et al. .................. 600/310 |
| 2006/0253007 A1 | 11/2006 | Cheng et al. |
| 2007/0088214 A1 | 4/2007 | Shuros et al. |
| 2007/0092862 A1 * | 4/2007 | Gerber .................. 435/4 |
| 2007/0093702 A1 | 4/2007 | Yu et al. |
| 2007/0142715 A1 | 6/2007 | Banet et al. |
| 2007/0185393 A1 | 8/2007 | Zhou et al. |
| 2007/0244398 A1 | 10/2007 | Lo et al. |
| 2007/0265533 A1 | 11/2007 | Tran |
| 2007/0276261 A1 | 11/2007 | Banet et al. |
| 2007/0276632 A1 | 11/2007 | Banet et al. |
| 2007/0299318 A1 | 12/2007 | Chen et al. |
| 2008/0027323 A1 | 1/2008 | Freiburger |
| 2008/0077026 A1 | 3/2008 | Banet et al. |
| 2008/0082004 A1 | 4/2008 | Banet et al. |
| 2008/0114220 A1 | 5/2008 | Banet et al. |
| 2008/0195043 A1 * | 8/2008 | Schwach et al. .................. 604/116 |
| 2008/0221399 A1 | 9/2008 | Zhou et al. |
| 2008/0221461 A1 | 9/2008 | Zhou et al. |

FOREIGN PATENT DOCUMENTS

| | | |
|---|---|---|
| WO | WO01/85014 | 11/2001 |
| WO | WO03/015838 | 2/2003 |
| WO | WO 2006/113748 | 10/2006 |
| WO | WO 2007/035934 | 3/2007 |
| WO | WO 2007/066343 | 6/2007 |
| WO | WO 2007/122375 | 11/2007 |

OTHER PUBLICATIONS

Office Action dated Dec. 22, 2010, in commonly owned U.S. Appl. No. 12/119,339.

Chemla et al., Blood flow acceleration in the carotid and brachial arteries of healthy volunteers: respective contributions of cardiac performance and local resistance, 1996, Fundam Clin Pharmacol, 10, pp. 393-399.

Tahmasebpour et al., Sonographic Examination of the Carotid Arteries, 2005, RadioGraphics, 25, pp. 1561-1575.

Office Action dated Oct. 7, 2011, in commonly owned U.S. Appl. No. 12/119,339, 20 pgs.

Office Action dated Dec. 21, 2011, in commonly owned U.S. Appl. No. 12/206,885, 14 pgs.

Office Action dated Dec. 15, 2011, in commonly owned U.S. Appl. No. 12/119,325, 12 pgs.

International Search Report and the Written Opinion of the International Searching Authority for PCT/IB 09/06081, 7 pages, Mar. 16, 2010.

* cited by examiner

METHOD AND SYSTEM FOR MONITORING A HEALTH CONDITION

CROSS-REFERENCE TO RELATED APPLICATIONS

The present application claims priority to and is a continuation-in-part of Israel Patent Application No. 185609 filed Aug. 30, 2007, titled "MULTI FUNCTION SENSSOR," and International Patent Application No. PCT/IL2006/001416 filed Dec. 10, 2006, titled "IMPLANTABLE BIOSENSING DEVICE AND HEALTH MONITORING SYSTEM AND METHOD INCLUDING SAME," which claims the benefit of U.S. Provisional Patent Application Ser. No. 60/748,218 filed Dec. 8, 2005, titled "WIRELESS INTEGRATED TRANSMITTER AND SENSOR," the disclosures of which are expressly incorporated by reference herein.

The present application is related to U.S. Utility patent application Ser. No. 12/119,315 titled "OPTICAL SENSOR APPARATUS AND METHOD OF USING SAME" filed on even date herewith, (hereinafter, "the Optical Sensor Apparatus application"), U.S. Utility patent application Ser. No. 12/119,339 titled "DOPPLER MOTION SENSOR APPARATUS AND METHOD OF USING SAME" filed on even date herewith, (hereinafter, "the Doppler Motion Sensor application"), and U.S. Utility patent application Ser. No. 12/119,325 titled "INTEGRATED HEART SENSING DEVICE AND METHOD OF USING SAME" filed on even date herewith, (hereinafter, "the Integrated Device application"), the entire disclosure of each application being expressly incorporated by reference herein.

FIELD OF THE INVENTION

The present invention relates to health monitoring systems and methods and, more specifically, to systems and methods including devices for monitoring cardiac behaviour.

BACKGROUND AND SUMMARY OF THE INVENTION

Cardiovascular disease is a large, growing health problem world wide. Some studies indicate that approximately 15% of the Western World suffers from one or more cardiovascular disease. In the United States, nearly 25% of the population is affected, resulting in more than six million hospitalizations every year.

Various devices exist for monitoring certain parameters relating to cardiac performance. In some instances, in vivo parameters of a patient may need to be monitored over a period of time. Heart arrhythmias are changes in the normal sequence of electrical impulses that cause the heart to pump blood through the body. Continuous monitoring may be required to detect arrhythmias because abnormal heart impulse changes might only occur sporadically. With continuous monitoring, medical personnel can characterize cardiac conditions and establish a proper course of treatment.

One prior art device that measures heart rate is the "Reveal" monitor by Medtronic (Minneapolis, Minn., USA). This device comprises an implantable heart monitor used, for example, in determining if syncope (fainting) in a patient is related to a heart rhythm problem. The Reveal monitor continuously monitors the rate and rhythm of the heart for up to 14 months. After waking from a fainting episode, the patient places a recording device external to the skin over the implanted Reveal monitor and presses a button to transfer data from the monitor to the recording device. The recording device is provided to a physician who analyzes the information stored therein to determine whether abnormal heart rhythm has been recorded. The use of the recording device is neither automatic nor autonomic, and therefore requires either the patient to be conscious or another person's intervention to transfer the information from the monitor to the recording device.

Another known type of implantable sensing device is a transponder-type device, in which a transponder is implanted in a patient and is subsequently accessed with a hand-held electromagnetic reader in a non-invasive manner. An example of the latter type of device is described in U.S. Pat. No. 5,833,603.

In many circumstances, medical personnel are interested in collecting a variety of different types of data relating to the behaviour of the heart and the condition of the patient. Moreover, as mentioned above, it is desirable to obtain as much relevant data as possible without requiring the patient to visit a health care provider (HCP). Relevant information may include the oxygen saturation level of blood flowing through the aorta, blood pressure, heart rate, blood flow, stroke volume, cardiac output, the electrical activity of the heart (for generating electrocardiogram (ECG) data), and body temperature.

A method and system for monitoring a health condition are disclosed herein. In one embodiment of the system according to the invention, the system includes a monitoring device, a patient monitoring application, and a data store. The monitoring device includes a Doppler sensor, an optical sensor, and a computing device. The sensors and the computing device are enclosed in a housing. The patient monitoring application receives parameter values from the monitoring application and stores them in the data store.

In one embodiment, a method for monitoring a health condition is provided. The method includes the steps of providing a monitoring device as described in the paragraph immediately above and computing one or more hemodynamic parameters with the monitoring device. The method further includes the steps of diagnosing a health condition based on the hemodynamic parameters and performing a function responsive to the health condition.

In another embodiment, the method for monitoring a health condition includes the steps of providing a monitoring device as described above and further including a communication device. The method further includes the steps of transmitting a command to the monitoring device and performing a function responsive to the command.

The features of this invention, and the manner of attaining them, will become more apparent and the invention itself will be better understood by reference to the following description of embodiments of the invention taken in conjunction with the accompanying drawings.

Figure 1:
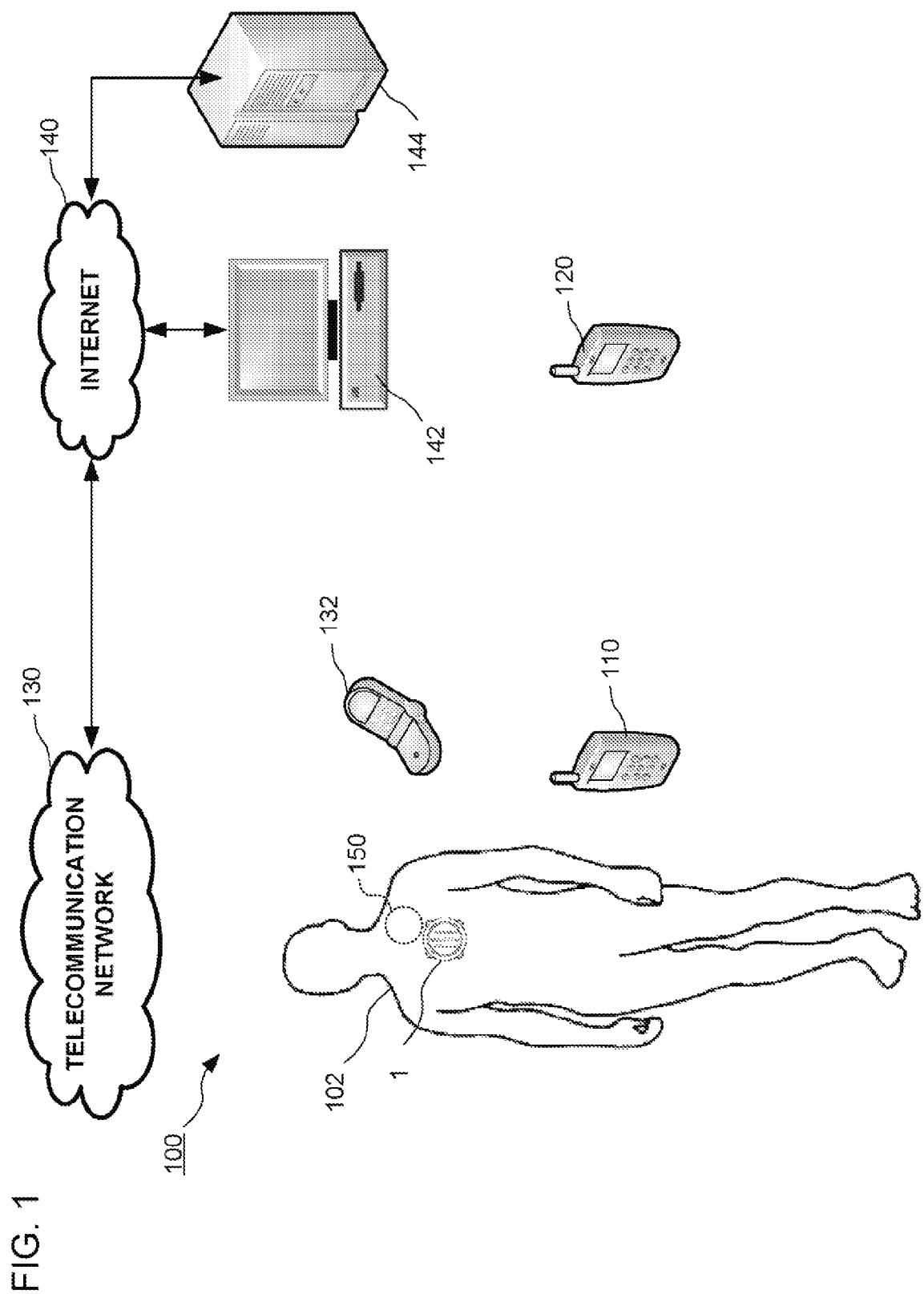
FIGS. 1 and 2 are schematic views of a system according to one embodiment of the present invention.

Corresponding reference characters indicate corresponding parts throughout the several views. Although the drawings represent embodiments of the present invention, the drawings are not necessarily to scale and certain features may be exaggerated in order to better illustrate and explain the present invention. The exemplifications set out herein illustrate embodiments of the invention in several forms and such exemplification is not to be construed as limiting the scope of the invention in any manner.

DETAILED DESCRIPTION OF EMBODIMENTS OF THE INVENTION

The embodiments discussed below are not intended to be exhaustive or limit the invention to the precise forms disclosed in the following detailed description. Rather, the embodiments are chosen and described so that others skilled in the art may utilize their teachings.

Figure 2:
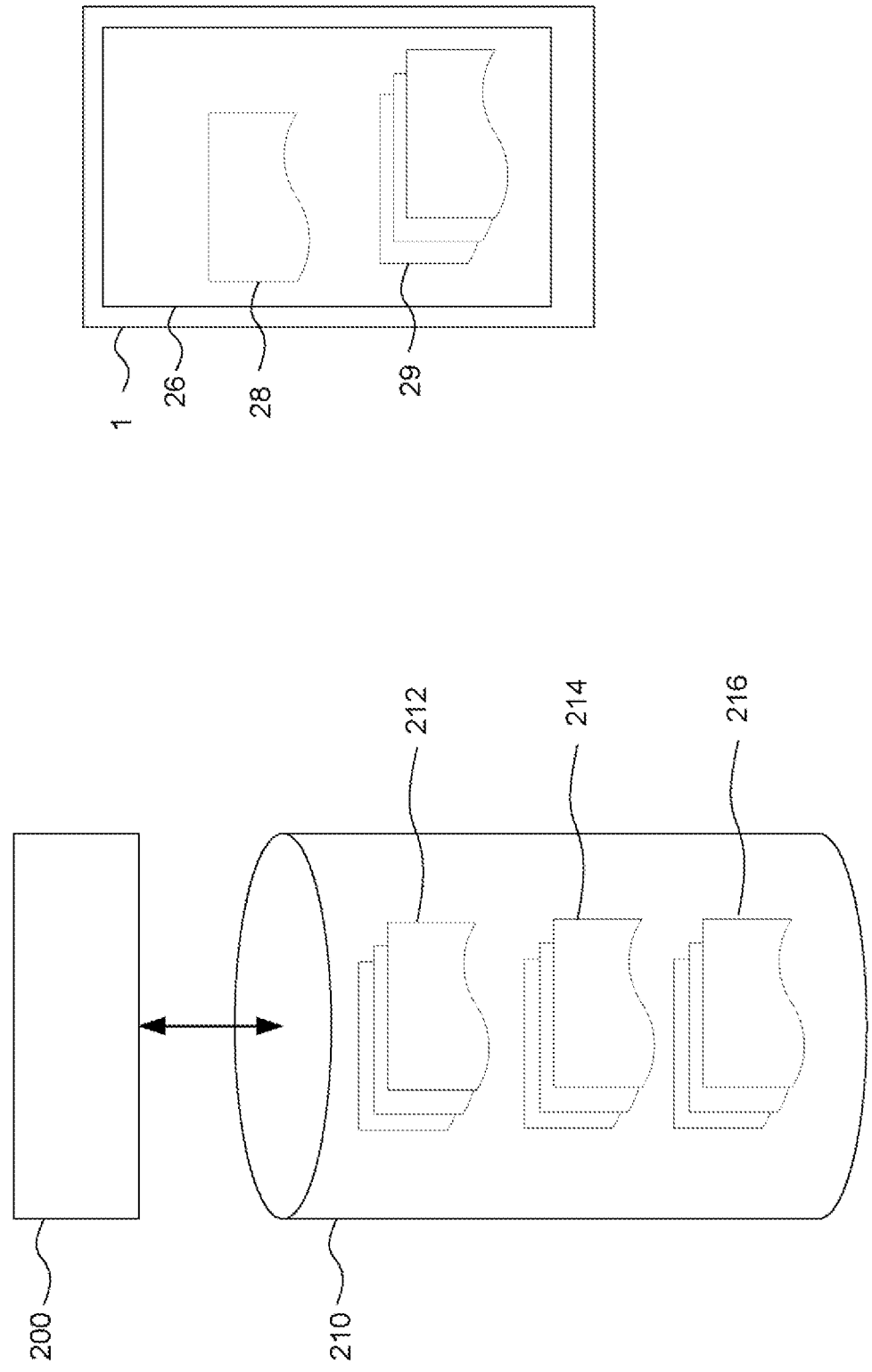

FIGS. 1 and 2 illustrate a system according to one embodiment of the invention. System 100 comprises a monitoring device 1 positioned on a patient 102, and an external communication device 120, exemplified as a personal digital assistant or Blackberry device. External communication devices may be any devices capable of receiving wireless or internet communications, such as communication devices 110, 132, and 142, exemplified as a relay unit, phone, and computer, respectively. Communication devices 120 and 132 and, optionally, 110, transfer information wirelessly through telecommunication network 130. Communication device 110 may also include a Bluetooth adapter or another adapter for communicating wirelessly with monitoring device 1 without using telecommunication network 130. Telecommunication network 130 is operably connected to the internet, represented by numeral 140, which transfers information from the telecommunication network to communication device 142. In one embodiment, system 100 further includes a website (not shown) containing webpages and residing in a server 144. In another embodiment, system 100 also includes a cardiac device 150 adapted to provide a treatment to the heart of patient 102.

System 100 includes a patient management application 200 and a data store 210. Patient management application 200 is a program configured to receive data from monitoring device 1 and other computing devices and to store data in data store 210. Patient management application 200 may reside in server 144. Patient management application 200 may be a client/server application with client programs residing in communication devices accessible through the internet. Data store 210 stores data pertaining to patients 102. Data may include a patient profile 212 including patient information such as, for example, address, insurance information, contact information, and device identification information for associating patient 102 with a specific monitoring device 1 and for enabling access to the sensing device. Data may also include values 214 comprising reference, measurement and parameter values retrieved from an associated monitoring device 1. Patient management application 200 may display values in a variety of ways to assist the HCP in managing the patient's health. Data may also include protocols 216.

Patient management application 200 has many functions. It retrieves data from monitoring device 1. It also updates reference values and protocols. It also transmits commands to monitoring device 1. In one embodiment, patient management application 200 sends commands to monitoring device 1 and monitoring device 1 performs functions responsive to the commands. In another embodiment, an HCP uses an external communication device to communicate with client management application 200 and client management application 200 communicates with monitoring device 1 responsive to the HCP communications. In another embodiment, an HCP accesses patient management application 200 through a website accessible via the internet.

Figure 3:
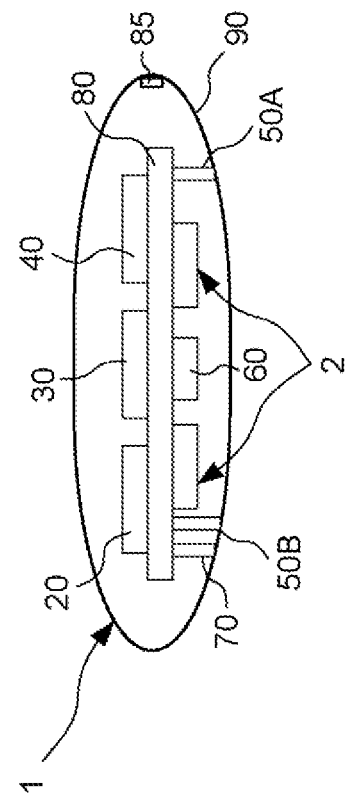
FIG. 3 is a schematic side view of a monitoring device according to one embodiment of the present invention.

FIG. 3 depicts monitoring device 1 including, generally, a plurality of components. One or more of the components may be incorporated in monitoring device 1 to suit the application of a method according to the invention. Monitoring device 1 may include a computing device 20, a communication device 30, an energy storage device 40, an optical sensor assembly 2, an ECG sensor including probes 50A and 50B (hereinafter collectively referred to as ECG sensor 50), a Doppler sensor 60, and a temperature sensor 70, each of the components mounted on a board 80 and being in electronic communication with computing device 20. The components are enclosed in a housing 90.

System 100 operably connects monitoring device 1 with one or more communication devices adapted to exchange data with monitoring device 1. Data includes commands, measurement, parameter and reference values, and protocols. Monitoring device 1 acquires measurement values, processes them according to a protocol, which in many cases involves comparing them to reference values and diagnostic profiles to diagnose abnormal conditions, and then performs a function according to a response profile based on the diagnosis.

Commands are instructions provided from an external communication device to computing device 20. Generally, commands are instructions for performing a function. Functions include transmitting data, performing a treatment, updating reference values, and updating protocols.

Reference values represent a normal or stable condition of a patient. Monitoring device 1 may be programmed with reference values or may be programmed to collect measurements upon placement of the device on patient 102 and to store the initial measurements or parameters as reference values. As explained in more detail below with reference to computing device 20, parameter values include hemodynamic parameters such as pulse rate, oxygen saturation, cardiac output, and blood pressure, and also temperature.

Reference values may include target values and acceptable variation ranges or limits. Parameter values may indicate an abnormality when they fall outside reference target values or ranges. In some embodiments, parameter values may produce a statistic such as, for example, a moving average, and an abnormality would be detected when the parametric statistic differs from a reference statistic by more than an expected amount.

One abnormal medical condition is cardiac arrhythmia. Computing device 20 may be configured to perform an analysis of the measurement values to determine, for example, whether the cardiac rhythm is irregular indicating arrhythmia. Other abnormal conditions include low oxygen saturation, low cardiac output, and high or low blood pressure. Other abnormal conditions may depend on combinations of various hemodynamic parameter values.

Protocols include diagnostic and response profiles. Diagnostic profiles provide computing device 20 decision criteria for diagnosing abnormal conditions. Response profiles provide computing device 20 instructions for performing functions responsive to diagnosis. Initially, one or more protocols may be programmed into monitoring device 1. A response profile in a first protocol may instruct computing device 20 to switch to a second protocol in response to an abnormal condition. In one embodiment, protocols may be downloaded to computing device 20 through communication device 30.

1. Monitoring Device

Throughout this application, references made to monitoring device 1 refer to the monitoring device 1 described in the Integrated Device application incorporated herein by reference above. Also, references made to optical sensor assembly 2 refer to the optical sensor assembly 2 described in the Optical Sensor Apparatus application incorporated herein by reference above. Furthermore, references to the Doppler sensor 60 refer to the Doppler sensor 60 described in the Doppler Motion Sensor application incorporated by reference above. The full description of the monitoring device 1, optical sensor assembly 2 and Doppler sensor 60 will not be repeated in this application.

By communication signal is meant a signal that has one or more of its characteristics set or changed to encode information in the signal. By way of example, and not limitation, communication signals include acoustic, RF, infrared, other wireless media, and combinations of any of the above. Relay unit 110 is located externally of the patient's body, e.g. clipped to the patient's belt. Relay unit 110 may include a receiver for receiving the transmissions from communication device 30, and a transmitter for re-transmitting the communication signal to another external communication device. Relay unit 110 may also be stationary and hardwired for connection to the internet or direct connection to a healthcare provider's computer. Likewise, relay unit 110 may receive a communication signal from a healthcare provider and transmit the signal to communication device 30.

Optical sensor assembly 2 includes a plurality of photon emitters and a plurality of photon detectors for detecting a plurality of optical signals. The emitters and detectors face the aorta. Computing device 20 operates the plurality of emitters and detectors and processes the plurality of optical signals to obtain optical measurement values representing the location and size of the aorta and the oxygen saturation of the blood flowing through the aorta.

Doppler sensor 60 emits and detects a plurality of ultrasonic waves. Computing device 20 also operates Doppler sensor 60 and, with the aid of the optical measurement values obtained using optical sensor assembly 2, processes the plurality of ultrasonic waves to obtain Doppler measurement values representing heart rate, blood flow, stroke volume, blood pressure, and cardiac output.

ECG sensor 50 detects the electrical signals which cause the heart to pump. Temperature sensor 70 measures the temperature of the patient. Energy storage device 40 powers computing device 20, the various sensors, and communication device 30 which is configured to transmit the collected data, or information relating to the collected data, according to various embodiments of a method disclosed herein. The sensors, computing device 20, communication device 30, and energy storage device 40 are enclosed in a housing 90.

Integrating the plurality of sensors and other components mentioned above in monitoring device 1 permits a single device, mounted at one location on the patient's body, to accurately measure a comprehensive set of parameters relating to the behaviour of the heart, including cardiac output. Moreover, monitoring device 1 may perform analyses of the parameters and perform functions in response to the "on-board" analyses, as opposed to other sensing devices that export raw data for analysis by another device. As indicated above, monitoring device 1 also communicates with other devices, wirelessly or otherwise, providing information and receiving commands and data. As such, monitoring device 1 collects, analyzes, and communicates data without any human intervention.

By "patient" it is meant a person or animal. In one embodiment according to the invention, monitoring device 1 is implanted subcutaneously in the patient's body. It should be understood, however, that monitoring device 1 may be implanted at different locations using various implantation techniques. For example, monitoring device 1 may be implanted within the chest cavity beneath the rib cage. Housing 90 may be formed in the shape of a circular or oval disc, with dimensions roughly the same as two stacked quarter dollar coins. More specifically, housing 90 may be approximately three centimeters in diameter and approximately one centimeter thick. Of course, housing 90 may be configured in a variety of other shapes and sizes, depending upon the application. Optical sensor assembly 2, Doppler sensor 60, ECG sensor 50, and temperature sensor 70 are positioned facing inwardly while an energy coupler component of energy storage device 40 faces outwardly.

Monitoring device 1 may be integrated with an implanted cardiac device 150 such as a pacemaker, a Cardiac Resynchronization Therapy (CRT) device, an implantable cardioverter defibrillator (ICD), etc. In such an embodiment, monitoring device 1 may communicate with the implanted cardiac device and provide information from the implanted cardiac device as well as from its own sensors to external devices. As many implanted cardiac devices are currently well-understood and routinely prescribed, integration of monitoring device 1 into such other devices may provide an effective means for achieving market acceptance.

The above-described integration may be achieved by combining the components of monitoring device 1 and the cardiac device. If the cardiac device includes a computing device, for example, the algorithms that carry out the functions according to the invention may be incorporated with the computing device of the cardiac device instead of adding a second computing device. In a similar manner, energy storage and communication devices may be combined to avoid duplication and lower cost.

Monitoring device 1 may be positioned externally to the patient's body. A support member is provided to support monitoring device 1 externally to the body. The support member may be permanently or temporarily coupled to monitoring device 1. The support member may comprise an adhesive layer for adhesively coupling the support member to the patient's body or may comprise a belt, which may be elastic, for holding monitoring device 1 against the patient's body.

Monitoring device 1 may be implanted or positioned on the patient with the aid of an external mapping system such as an ultrasound machine. Proper placement ensures that a vessel of interest, e.g. the aorta, is located within the sensing range of the various sensors of monitoring device 1. For example, monitoring device 1 may be positioned on the chest or back of the patient in a location that reduces interference by the ribs of the measurements acquired in the manner described herein.

Figure 4:
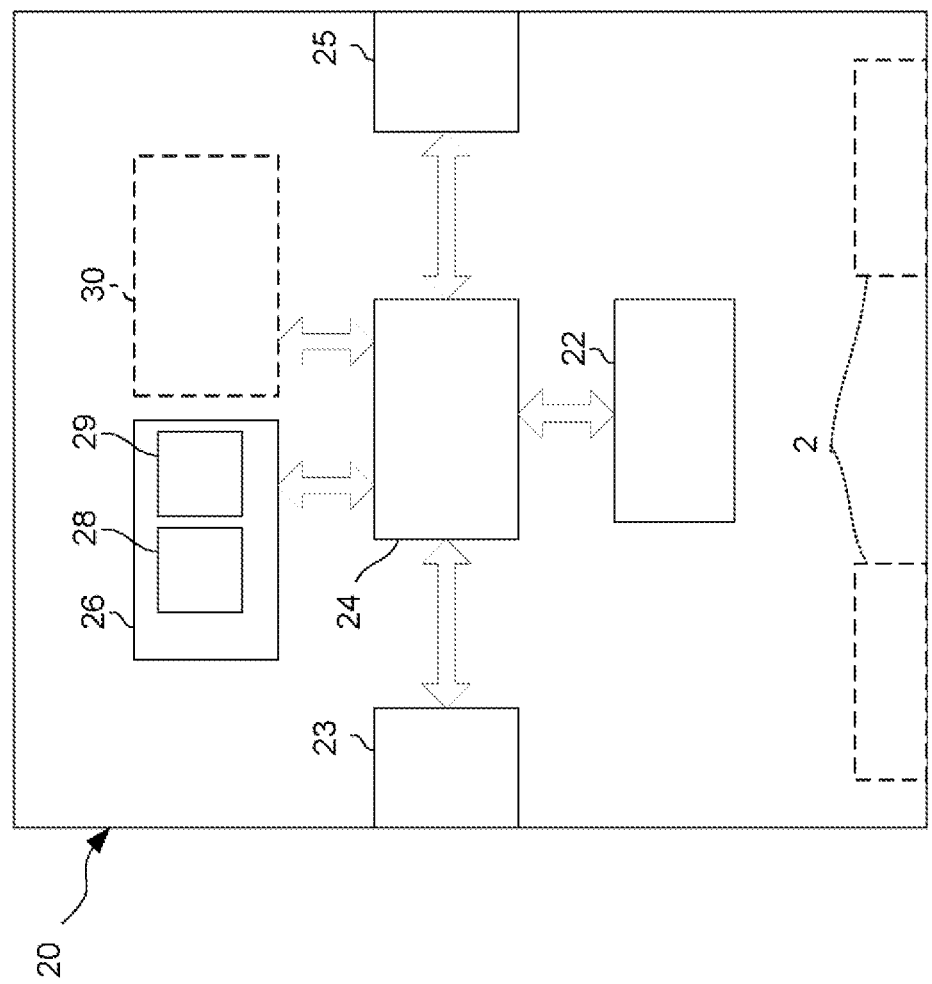
FIG. 4 is a conceptual view of a computing device according to one embodiment of the present invention.

Computing device 20 comprises a plurality of components. While components are described herein as if they were independent components, the components may be combined in a single device such as an application specific integrated circuit. As shown in FIG. 4, computing device 20 includes an A/D converter 22 (which also converts optical signals to digital signals), a processor 24, a memory 26, a program 28, a data 29, inputs 23, and outputs 25. Memory 26 may include, but is not limited to, RAM, ROM, EEPROM, flash memory or other memory technology. A/D converter 22, processor 24 and memory 26 may be constructed in an integrated circuit. The integrated circuit may further include emitter array 100, detector array 200, and communication device 30.

Program 28 represents computer instructions directing processor 24 to perform tasks responsive to data 29. Program 28 resides in memory 26. Data 29 includes values and protocols and also resides in memory 26. Reference data may be stored in ROM or it may be stored in RAM so that it may be modified over time, either in response to external inputs or in response to characteristics of measurement data collected over time. Protocols for responding to measurement values may also be provided. Protocols may be stored in permanent memory or may be stored in non-permanent memory such as RAM.

Computing device 20 may be configured to cause communication device 30 to transmit an alert if an abnormal condition is detected, particularly a condition determined to be a serious or dangerous condition. A diagnosis profile in an active protocol provides criteria to determine whether a condition is normal or abnormal, and if abnormal, the degree of severity. A response profile in the protocol provides criteria to respond to the diagnosis. Transmission of an alert is one example of a response. The alert may be used to actuate an alarm or to alert the patient to take remedial action. A remedial action may be terminating or reducing physical activity. The alert may also provide global positioning (GPS) information to an emergency service. Referring to FIG. 1, the abnormal condition, when found to be present, may also be displayed on external communication devices 110, 120, 132 and or 142. The alert may comprise a text message or a code corresponding to the condition. According to a protocol, computing device 20 may also initiate a new measurement cycle and measure on a continuous basis in response to the detection of an abnormal condition.

Computing device 20 may also initiate a treatment according to a response profile or responsive to a command. Monitoring device 1 may receive, through communication device 30, an external command to perform a treatment in response to the alert. Optionally, based on the protocol, an abnormal condition may also be used to direct a device adapted to provide treatment to deliver such treatment. Treatment may include, for example, an electric shock or a drug delivery.

Parameter values and/or other information may be communicated to an external device. The parameter values may be stored in memory 26 and transmitted wirelessly by communication device 30. The communication signal from communication device 30 may be activated on a periodic basis (e.g., once per day, once per week, etc.), in response to an abnormal condition, in response to an externally received command, whenever memory usage exceeds a predetermined amount, or whenever the energy storage level is determined to be low, the latter two conditions established to prevent data loss as a result of memory overflow or energy loss. It should also be understood that monitoring device 1 may include communication devices in addition to communication device 30. For example, where communication device 30 is a cellular modem, monitoring device 1 may also include a backup Bluetooth or RF communication device. Such a backup device may be desirable in situations where, after one or more attempts, it becomes apparent that the cellular modem is unable to transmit information (e.g., due to low available power, poor network coverage, etc.). In such a situation, computing device 20 may activate the backup communication device to transmit information or an alert to an alternate external communication device.

Alternatively or in addition to the above-described transmissions, computing device 20 may be programmed to respond to requests for data received by communication device 30 (e.g., from a health care provider) by causing communication device 30 to transmit the requested data or information representing the requested data.

The communication signal may be received by equipment near the patient to alert the patient to the condition, or received remotely (such as over a network) by a healthcare provider, relative, or other predetermined recipient.

It should be understood that each of or some of optical sensor assembly 2, Doppler sensor 60, ECG sensor 50, and temperature sensor 70 may be modular in design. As such, a plurality of different Doppler sensors 60, for example, may be produced to have different performance characteristics (e.g., different output frequencies). Depending upon the application, any of the plurality of the sensors may be installed in monitoring device 1 to achieve the desired performance. Once monitoring device 1 is equipped with the selected sensors, computing device 20 may be programmed to adapt the various algorithms to accommodate the selected sensors. In this manner, a basic monitoring device 1 including computing device 20, communication device 30, etc., may be "custom" built with any of a variety of sensors and programmed to operate with the selected sensors.

It should be understood that while optical sensor assembly 2, Doppler sensor 60, and temperature sensor 70 are described herein as being activated to obtain measurements relatively infrequently (at least under normal conditions) to conserve power, as battery technology improves, the frequency of activation of these sensors may be increased. Also, where monitoring device 1 is worn externally, connector 85 may be used to supply power to sensing device 85, thereby eliminating the power consumption concern and permitting frequent, or even continuous, operation of these sensors. Furthermore, connector 85 may be utilized to operably connect other sensors to monitoring device 1.

In one embodiment of the invention, communication device 30 is a two-way communication device, e.g. via the cellular telephone system and/or the GPS satellite system, such as NOKIA model number KNL1147-V. In an alternate embodiment, communication device 30 is capable of transmitting information, but does not receive information or commands.

A system for recharging energy storage device 40 may be provided in one embodiment according to the invention. Computing device 20 receives energy from energy storage device 40. Energy storage device 40 includes an energy storage component such as a battery. Optionally, monitoring device 1 may also include an energy coupler for receiving energy from an external source to charge energy storage device 40.

One example of an energy coupler is an electromagnetic device, such as induction coils, for receiving external electromagnetic signals and converting them into electrical energy for recharging the energy storage component. An external electromagnetic device generates electromagnetic signals which are received and converted into electrical energy by energy storage device 40. Energy storage device 40 may provide a charge signal to computing device 20. Computing device 20 may compare the charge signal to a reference charge signal and initiate a low charge communication signal for alerting the patient and/or healthcare providers. Alternatively, a detector, such as a voltage sensor, may be used to monitor the charge of energy storage device 40 and provide a signal to computing device 20 when the charge falls below a threshold. The electromagnetic device may be placed near monitoring device 1 to charge energy storage device 40.

Energy may instead, or additionally, be provided in the form of ultrasonic vibrations. For example, a piezoelectric transducer may be included in monitoring device 1. An ultrasonic vibration may be provided externally. The transducer generates electricity when driven by ultrasonic vibrations. As indicated herein, energy or power may also be provided to monitoring device 1 through connector 85.

2. Diagnosis and Operation

It is important to diagnose heart conditions properly. Improper diagnosis may lead to improper treatment which may result in the death or severe permanent disability of the patient. Due to the potential harm, it is natural to employ abundant caution. However, abundant caution raises treatment costs which, in aggregate, impose a cost on society. Proper diagnosis may reduce treatment costs while also likely improving the condition of the patient.

Heart failure can result from any structural or functional cardiac disorder that impairs the ability of the heart to pump a sufficient amount of blood through the body. Heart failure is caused by any condition which reduces the efficiency of the myocardium through damage or overloading, including myocardial infarction (in which the heart muscle is starved of oxygen and becomes damaged) and hypertension (which increases the force of contraction needed to pump blood and often causes the heart muscle to become thicker, resulting in altered function of the muscle).

In addition to monitoring and responding instantaneously to abnormalities, it is important to develop a physiological history of a patient with chronic heart failure to prevent potentially fatal incidents. Heart failure can be chronic and congestive, or decompensated. Decompensated heart failure occurs when a patient with chronic heart failure develops acute symptoms. Symptoms may be based on the side of the heart, right or left, that is involved, the type of failure, either diastolic or systolic, whether the abnormality is due to low cardiac output, and the degree of functional impairment conferred by the abnormality (based on functional classification).

There is no universally accepted diagnostic standard for heart failure. Various standards include the Framingham, Boston and Duke criteria (named after related studies). The New York Heart Association Functional Classification classifies the severity of symptoms and can be used to assess response to treatment. Patients in Class I experience no limitations in any activities and experience no symptoms from ordinary activities. Patients in Class II experience slight, mild limitation of activity but are comfortable at rest or with mild exertion. Patients in Class III experience marked limitations of any activity and are comfortable only at rest. Patients in Class IV experience discomfort with any physical activity and experience symptoms at rest. A patient's classification may be programmed and used to identify a protocol to respond to a diagnosis.

Over time, conditions that increase the heart's workload will produce changes to the heart itself so it is important to monitor heart performance for changes that may lead to re-classification of a patient with corresponding changes in treatment. Heart changes include reduced contractility, or force of contraction, due to overloading of the ventricle; reduced stroke volume; increased end systolic volume (usually caused by reduced contractility); decreased end diastolic volume (usually caused by impaired ventricular filling); reduced spare capacity; and increased heart rate stimulated by increased sympathetic activity in order to maintain cardiac output.

The predominant respiratory symptom of left side failure is shortness of breath on exertion (dyspnea) or at rest, and easy fatigueability. Other symptoms include increasing breathlessness on reclining and severe breathlessness during sleep, usually several hours after going to sleep. Poor circulation to the body leads to dizziness and confusion. The right side of the heart pumps deoxygenated blood and right side failure leads to congestion of peripheral tissues. Heart failure may decompensate easily as a result of intercurrent illness, myocardial infarction, arrhythmias, and uncontrolled hypertension, among other causes. General signs indicating possible heart failure include a laterally displaced apex beat (as the heart is enlarged), a gallop rhythm (additional heart sounds) in case of decompensation, and heart murmurs which may indicate valvular heart disease, either as a cause (e.g. aortic stenosis) or as a result of the heart failure. An echocardiogram may be used to identify these general signs of possible heart failure.

Heart failure caused by systolic dysfunction is the failure of the pump function of the heart. It is characterized by a decreased ejection fraction (less than 50%, and often significantly lower). Normally, the ejection fraction should be between 50% and 70%. The strength of ventricular contraction is attenuated and inadequate for creating an adequate stroke volume, resulting in inadequate cardiac output. Because the ventricle is inadequately emptied, ventricular end-diastolic pressure and volumes increase. On the left side of the heart, the increased pressure causes pulmonary edema. On the right side of the heart, the increased pressure results in dependent peripheral edema. Doppler sensor 60 may be used to determine the stroke volume (SV), an important determinant of cardiac function.

Heart failure caused by diastolic dysfunction is the failure of the ventricle to adequately relax and typically denotes a stiffer ventricular wall. This causes inadequate filling of the ventricle which results in an inadequate stroke volume. The failure of ventricular relaxation also results in elevated end-diastolic pressures which results in edemas. Diastolic dysfunction may not manifest itself except in physiologic extremes if systolic function is preserved, thus, a patient may be completely asymptomatic at rest. However, diastolic dysfunction is hypersensitive to increases in heart rate and blood pressure. Sudden bouts of tachycardia can be caused by exertion, fever, or dehydration. ECG sensor 50 may track increases in heart rate by comparing heart rate to reference values. Elevated blood pressures may be identified with Doppler sensor 60 in a similar manner. The parameters may be correlated in time to potentially diagnose diastolic dysfunction.

Hypothetical scenarios will now be described to exemplify protocols responsive to a cardiac failure event. The scenarios are based on hypothetical symptoms.

In the first case, the patient is 65 years old and suffered an anterior myocardial infarction two years prior to the event. During the year prior to the event, he suffered from congestive heart failure, characterized by dyspnoea on mild effort, fatigue and rare events of shortness of breath at rest. His New York Heart Association functional class was defined as II-III. He received medications including ACE inhibitors, beta blockers and spironolactone which resulted in some functional improvement. After experiencing general weakness and some shortness of breath, the patient called his HCP and communicated his symptoms.

In a base scenario, the patient does not benefit from using monitoring device 1. Under normal conditions, the symptoms would almost certainly lead the HCP to suspect decompensated heart failure. A typical response would be to send a mobile intensive care unit to collect the patient. If decompensated heart failure did not exist, collecting the patient would be unnecessary. However, if decompensated heart failure did exist, and the patient arrived at the healthcare facility more than two or three hours after the event, late treatment may be dangerous and, occasionally, life threatening.

In the following alternative scenarios exemplifying different embodiments of a method according to the invention, the patient does benefit from using monitoring device 1. Prior to the event, the HCP programs monitoring device 1 with protocols corresponding to the patient's history and New York Heart Association functional class or another classification. The protocols may be updated from time to time.

In a first scenario, upon receiving the phone call the HCP accesses an external communication device to retrieve pulse rate data, through communication device 30, to determine whether any arrhythmia is present. Then, the HCP retrieves $O_2$ saturation measurements. A normal saturation (>98%) would almost certainly exclude a serious event. To complete the examination, the HCP instructs the patient, by telephone, to sit still for two to three minutes after which time the HCP commands monitoring device 1 to compute cardiac output and blood pressure. This information would be sufficient to determine whether the patient indeed suffers from decompensation. If he does not, an unnecessary trip to the healthcare facility may be avoided.

In this scenario, the HCP sends commands to monitoring device 1 using the external communication device. The HCP may select commands from patient management application 200 which may include a website dedicated to support such communications. Alternatively, the external communication device may be phone 132 and the commands may comprise dialing a phone number for accessing communication device 30, in this case a telephone modem, entering a numeric access code for accessing data on monitoring device 1, and subsequently entering a numeric code corresponding to a protocol for retrieving data. A protocol may refer to a single parameter or to more than one parameter. Monitoring device 1 responds to each command by transmitting a string of data.

Figure 5:
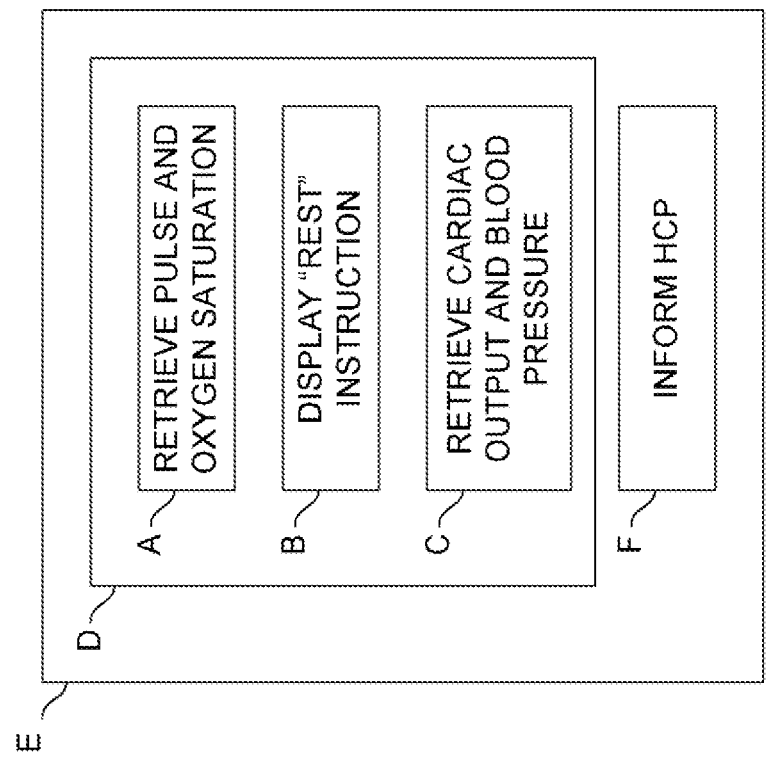
FIGS. 5 and 6 are conceptual representations of protocols for performing embodiments of a method according to the invention.

Referring to FIG. 5, an exemplary group of protocols are illustrated. The HCP activates a protocol A to retrieve pulse and oxygen saturation data. Because these parameters are obtained with ECG sensor 50 and optical sensor assembly 2, which are low power devices, obtaining these values does not consume much energy. If the patient has relay unit 110 including a display screen, a protocol B may also be activated instructing the patient to rest for two or three minutes. Finally, the HCP activates a protocol C to retrieve cardiac output and blood pressure values. These are obtained with the Doppler sensor 60 which consumes more energy than optical sensor assembly 2. Alternatively, the patient may have been resting already and the HCP might not need to wait before activating protocol C.

In a second scenario, exhibiting some automation, upon receiving the phone call the HCP accesses an external communication device to activate a diagnosis protocol D. Protocol D may then cause computing device 20 to (a) transmit pulse and oxygen saturation data, (b) wait and send a "wait" message to relay unit 110, and (c) transmit cardiac output and blood pressure data. In other words, protocol D automates activation of protocols A-C. The HCP may remain on the phone with the patient while transmitting the command to activate protocol D and receiving information on the external communication device. If the patient does not have a relay unit, the HCP may instruct the patient to rest.

In a third scenario, exhibiting more automation, the patient executes a command on the relay unit. Relay unit 110 may be a communication device capable of transmitting wireless commands to monitoring device 1. For example, relay unit 110 may include a button designated as a "panic" button which a patient or another person may press in case of concern. Upon experiencing the general weakness and shortness of breath, patient 102 presses the panic button which commands monitoring device 1 to activate a protocol E. Protocol E directs computing device 20 to activate protocol D and to also protocol F to inform the HCP that the panic button was pushed. The HCP may text-message relay unit 110 from a communication device with additional instructions for the patient or may take other discretionary actions. Protocol E saves the time required for the patient to call the HCP and for the HCP to activate protocol D.

Figure 6:
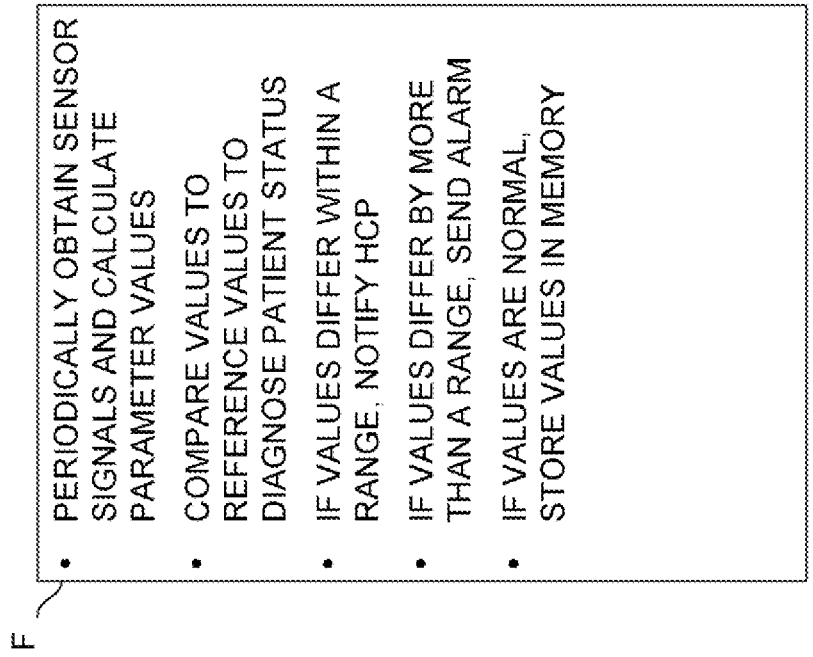

Referring to FIG. 6, in a fourth scenario exhibiting full automation, monitoring device 1 diagnoses an abnormality and performs a function according to a protocol F. A diagnosis profile in monitoring device 1 directs the device to monitor, at predetermined time intervals, changes in cardiac pulse rate, cardiac output, oxygen saturation, or combinations of changes in these parameters. The profile also directs the device to compare the changes to reference values and to signal an abnormal condition if the changes exceed a predefined amounts. A response profile directs the device to perform a function responsive to the abnormality. In one embodiment, monitoring device 1 sends a message or data to the HCP if values differ from reference values within a range. In another embodiment, monitoring device 1 sends an alarm to the HCP if values differ by more than a range, signifying an emergency. The alarm may also be sent to designated caretakers of the patient, or may even send an alarm to a healthcare facility, ambulance service or fire department. Additionally, monitoring device 1 may send a message to relay unit 110 which patient 102 may read. For example, the relay unit may display a message instructing the patient to sit, rest, drink water, etc.

In a second case, a 60 year old patient experiences an event 2 weeks after coronary bypass surgery. He has been well, already walking 45 minutes/day and starting to do some office work from home. He experiences palpitation, some shortness of breath and dizziness. The symptoms may be due to atrial flutter/fibrillation which is a common condition during the first several weeks after bypass surgery. Diagnosis in this case requires pulse, blood saturation, blood pressure and cardiac output data. If the data appears normal compared to reference values, the patient is instructed to rest and the heart parameters are checked again in one to two hours. The second check may be performed by the HCP without requiring a phone call to contact the patient. If all parameters are stable and the patient feels better—he can stay home.

In a third case, a patient has an implanted ICD (defibrillator). After waking up from an afternoon nap, the patient is somewhat confused and has some chest discomfort. He is worried that the ICD may have charged and that he may have had a serious arrhythmia.

In one scenario, monitoring device 1 is incorporated, either integrated or operably connected, into the ICD. If the ICD determines that defibrillation is appropriate, the ICD communicates the determination to monitoring device 1. Monitoring device 1 checks hemodynamic parameters (pulse, oxygen saturation, blood pressure, cardiac output) and verifies an abnormality indicating that defibrillation is appropriate or determines that it is not. If the latter, monitoring device 1 instructs the ICD to not charge. Monitoring device 1 might also transmit the event information to the HCP. The HCP could interrogate the device to collect the hemodynamic parameters and to determine whether an arrhythmia had indeed occurred. If no arrhythmia was detected and hemodynamic parameters are normal, no further investigation is necessary.

In another scenario, monitoring device 1 is not incorporated into the ICD. Monitoring device 1 may be programmed to detect when the ICD charges. The patient may initiate communication with the HCP by telephone, panic button, or any other means described above to determine whether the ICD charged. In another embodiment, the charge event is displayed in relay unit 110 for the patient to read. In other embodiments, other cardiac devices are operationally integrated with monitoring device 1 to improve their joint performance by combining features.

Figure 7:
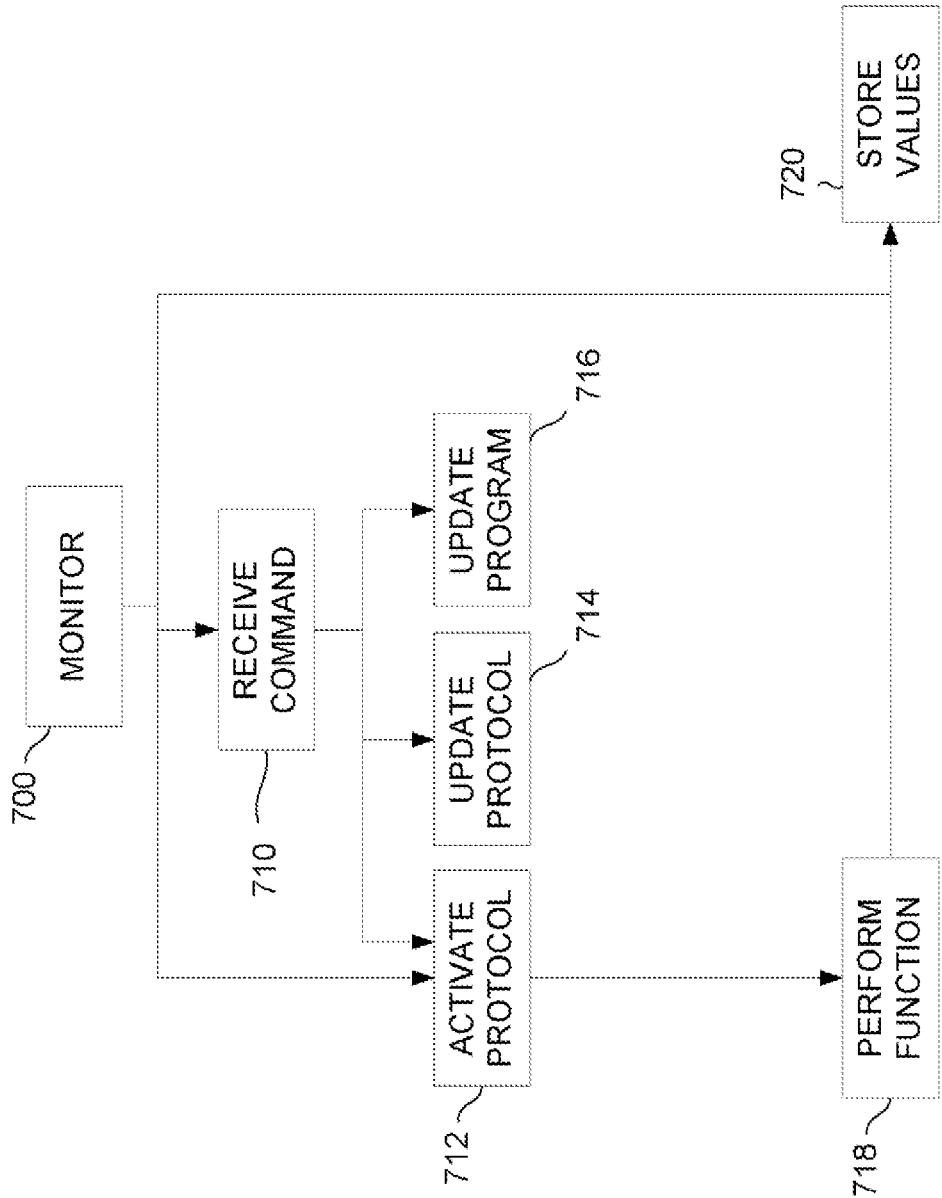
FIG. 7 is a flow-chart of a further embodiment of a method according to the invention.

FIG. 7 illustrates an embodiment of a patient management method according to one embodiment of the invention. Initially, an HCP sets up monitoring device 1 for use with patient 102. The HCP populates data store 210 with information relating to patient 102 including patient history, monitoring device identification, and other information. The HCP also selects protocols to download to monitoring device 1. Protocols may be downloaded using connector 85 while monitoring device 1 is docked in a docking station. Monitoring device 1 is positioned on the patient with the aid of an ultrasound machine. During the initial setup, the HCP may obtain baseline measurements and may store the measurements as reference values in computing device 20.

At step 700, monitoring device 1 monitors patient 102. Monitoring may be performed according to protocol F as described above or according to another protocol. Monitoring includes activating sensors to obtain measurement values, computing parameter values, comparing the values to reference values according to a protocol, and diagnosing a normal or abnormal condition. If values are outside a reference range, monitoring device 1 may proceed to step 712 or may initiate a new measurement cycle to verify the parametric data before diagnosing an abnormality. Otherwise, monitoring device 1 proceeds to step 720 and then returns to step 700.

At step 710, monitoring device 1 receives a command from an external communication device. A command may direct monitoring device 1 to transmit parameter values according to a protocol, or update a protocol, or update a program.

At step 712, monitoring device activates a protocol. The protocol may indicate which parameters to sense, how much data (minutes, hours, days) to acquire, and how frequently to continue measuring. The protocol is determined by the command received or responsive to the monitoring protocol from step 700. The external communication device may be computer 142. Computer 142 may include patient management application 200 or may access patient management application 200 through the internet. Patient management application 200 may provide an option menu showing available protocols and may also include security features for the protection of the patient's privacy as well as well-being. The external communication device may also be communication device 110, 120 and 132. In this step, monitoring device 1 activates the sensors which generate signals that are received by computing device 20. Computing device 20 conditions the signals and converts them to measurements, then analyzes the measurements and computes parameter values. Finally, computing device 20 performs additional instructions provided in the protocol.

In another embodiment, the communication device accesses monitoring device 1 directly without using a patient management application. The communication device may dial monitoring device 1 and provide commands via a keypad.

At step 714, monitoring device 1 executes a command for updating a protocol. Updating may involve changing the reference values that determine an abnormal condition or changing reference values that distinguish the severity of an abnormal condition, e.g. an emergency. Other updates include changing the sequence of steps or the responses in the response profile. In this step, additional protocols may be added. Protocols may be updated to reflect changing patient conditions, history or other factors.

At step 716, monitoring device 1 executes a command to update a program. A program may comprise modules including algorithms for processing signals from sensors. Modules may be updated to reflect newer modules with improved features. Additionally, modules may be updated to reflect the addition of external or additional sensors.

At step 718, monitoring device 1 performs a function. A function may include transmitting a communication signal, performing a treatment, or other functions specified in the response profile of the protocol. The response profile may indicate which parameters to transmit, how much data (minutes, hours, days) to transmit, and how frequently to continue measuring.

At step 720, monitoring device 1 stores measurement values. Values may be stored as a result of a protocol activated at step 712 or as a result of normal conditions. Step 720 may be performed, for example, once an abnormal condition has been detected so as to update a caregiver on a substantially real-time basis. Step 720 may also be performed at regular intervals, such as once a day, once a week, once a month, etc. Alternatively or in addition to these transmissions, computing device 20 may be programmed to respond to requests for data received by communication device 30 (e.g., from a health care provider) by causing communication device 30 to transmit the requested data or information representing the requested data.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A method for monitoring a health condition comprising:
    positioning a monitoring device in or on a patient, the monitoring device including
        an optical sensor for sensing a relative position of a vessel,
        a Doppler sensor for sensing a velocity of a fluid flowing in the vessel, and
        a computing device for operating the optical sensor and the Doppler sensor to obtain parameter values, the computing device including one or more protocols for diagnosing and responding to the health condition,
        an energy storage device to power the optical sensor, the Doppler sensor, and the computing device, and
        one housing, the energy storage device, the optical sensor, the Doppler sensor, and the computing device being enclosed in the one housing;
    by the monitoring device:
        computing one or more hemodynamic parameter, wherein the hemodynamic parameter includes one of oxygen saturation, stroke volume, blood pressure and cardiac output;
        diagnosing the health condition based on the one or more hemodynamic parameters; and
        performing a function responsive to the health condition.

2. The method of claim 1, wherein diagnosing the health condition is performed by the computing device based on a first protocol corresponding to the patient's medical history, the patient's medical history including a functional classification selected from a heart failure classification standard, for diagnosing and responding to a health condition to determine if the health condition is an abnormal condition, further comprising switching by the computing device to a second protocol upon determination of the abnormal condition.

3. The method of claim 1, wherein the monitoring device further includes a communication device, the method further comprising:
transmitting, by the communication device, at least one of the one or more hemodynamic parameters;
by a health care provider,
receiving the at least one hemodynamic parameter,
determining, based on the at least one hemodynamic parameter, whether an arrhythmia is present, and
receiving another of the at least one or more hemodynamic parameters, which is different from the at least one hemodynamic parameter.

4. The method of claim 1, wherein the function is performing a treatment, the function being performed by the monitoring device.

5. The method of claim 1, wherein the monitoring device further includes a communication device, wherein when the condition is normal, the function is communicating parameter values on a periodic basis, and when the condition is abnormal, the function is communicating parameter values on a continuous basis.

6. The method of claim 3, further comprising:
confirming, by the health care provider based on the another of the at least one or more hemodynamic parameters, whether the arrhythmia is present.

7. A method for monitoring a health condition comprising:
providing a monitoring device including
an optical sensor for sensing a relative position of a vessel,
a Doppler sensor for sensing a velocity of a fluid flowing in the vessel,
a computing device for operating the optical sensor and the Doppler sensor to obtain parameter values, the computing device diagnosing the health condition based on the parameter values,
a communication device coupled to the computing device;
an energy storage device to power the communication device, the optical sensor, the Doppler sensor, and the computing device, and
one housing, the energy storage device, the optical sensor, the Doppler sensor, the communication device, and the computing device being enclosed in the one housing,
transmitting a command to the monitoring device; and
by the monitoring device, performing a function responsive to the command, wherein the function is computing a parameter from the group comprising oxygen saturation, stroke volume, blood pressure, cardiac pulse and cardiac output.

8. The method of claim 7, wherein the function further comprises transmitting a parameter value.

9. The method of claim 7, wherein the computing device includes a diagnosis protocol for diagnosing a health condition and the function further comprises transmitting a parameter value from the parameter values according to the diagnosis protocol.

10. The method of claim 7, wherein the computing device includes a diagnosis protocol for diagnosing a health condition and the function further comprises updating the diagnosis protocol.

11. The method of claim 7, wherein the function further comprises initiating a treatment.

12. A method for monitoring a health condition comprising:
providing a monitoring device including
an optical sensor for sensing a relative position of a vessel,
a Doppler sensor for sensing a velocity of a fluid flowing in the vessel,
a computing device for operating the optical sensor and the Doppler sensor to obtain parameter values, the computing device diagnosing the health condition based on the parameter values,
a communication device coupled to the computing device;
an energy storage device to power the communication device, the optical sensor, the Doppler sensor, and the computing device, and
one housing, the energy storage device, the optical sensor, the Doppler sensor, the communication device, and the computing device being enclosed in the one housing,
transmitting a command to the monitoring device; and
by the monitoring device, performing a function responsive to the command,
wherein the function is initiating a treatment, and
wherein the treatment is an electric shock.

13. A method for monitoring a health condition comprising:
providing a monitoring device including
an optical sensor for sensing a relative position of a vessel,
a Doppler sensor for sensing a velocity of a fluid flowing in the vessel,
a computing device for operating the optical sensor and the Doppler sensor to obtain parameter values, the computing device diagnosing the health condition based on the parameter values,
a communication device coupled to the computing device;
an energy storage device to power the communication device, the optical sensor, the Doppler sensor, and the computing device, and
one housing, the energy storage device, the optical sensor, the Doppler sensor, the communication device, and the computing device being enclosed in the one housing,
transmitting a command to the monitoring device; and
by the monitoring device, performing a function responsive to the command,
wherein the function is initiating a treatment, and
wherein the treatment is delivering a drug.

14. A system for monitoring a health condition comprising:
a monitoring device including an optical sensor for sensing a relative position of a vessel, a Doppler sensor for sensing a velocity of a fluid flowing in the vessel, a computing device for operating the optical sensor and the Doppler sensor to obtain parameter values, the computing device diagnosing the health condition based on the parameter values, an energy storage device to power the optical sensor, the Doppler sensor, and the computing device, and one housing, the energy storage device, the optical sensor, the Doppler sensor, and the computing device being enclosed in the one housing; and
a patient monitoring application for transmitting data to the monitoring device and for receiving parameter values from the monitoring device, wherein the parameter values include one or more of oxygen saturation, stroke volume, blood pressure, and cardiac output; and
a data store for storing parameter values.

15. The system of claim 14, wherein the parameter values further comprise cardiac pulse.

16. The system of claim 14, further comprising an external communication device configured to receive information from the monitoring device and transmit the information to the patient monitoring application.

17. The system of claim 16, wherein the external communication device is configured to receive instructions from the patient monitoring application and to present the instructions with a display device.

18. The system of claim 16, wherein the external communication device includes a switch configured to, upon operation of the switch, communicate an emergency indicator to the patient monitoring application and transmit the parameter values.

19. The system of claim 18, wherein parameter values transmitted upon operation of the switch are operable to diagnose, by a health care provider, whether an arrhythmia is present.

* * * * *